US011904041B2

(12) United States Patent
Strand et al.

(10) Patent No.: US 11,904,041 B2
(45) Date of Patent: *Feb. 20, 2024

(54) LEAVE-ON ORAL CARE COMPOSITIONS

(71) Applicant: The Procter & Gamble Company, Cincinnati, OH (US)

(72) Inventors: Ross Strand, Singapore (SG); Yang Su, Beijing (CN); Yunming Shi, Beijing (CN); Thanigaivel Shanmugam, Beijing (CN); Xiaowei Li, Beijing (CN); Guannan Wang, Beijing (CN)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/899,834

(22) Filed: Jun. 12, 2020

(65) Prior Publication Data

US 2020/0390676 A1    Dec. 17, 2020

(30) Foreign Application Priority Data

Jun. 14, 2019  (WO) ................ PCT/CN2019/091272
Jun. 11, 2020  (WO) ................ PCT/CN2020/095595

(51) Int. Cl.
*A61K 8/73*     (2006.01)
*A61Q 11/00*    (2006.01)
*A61K 8/81*     (2006.01)
*A61K 8/67*     (2006.01)
*A61C 19/06*    (2006.01)

(52) U.S. Cl.
CPC ............ *A61K 8/735* (2013.01); *A61C 19/063* (2013.01); *A61K 8/673* (2013.01); *A61K 8/676* (2013.01); *A61K 8/678* (2013.01); *A61K 8/8147* (2013.01); *A61Q 11/00* (2013.01); *A61K 2800/30* (2013.01); *A61K 2800/87* (2013.01)

(58) Field of Classification Search
CPC ...... A61K 8/735; A61K 8/8147; A61K 8/676; A61K 8/673; A61K 8/678; A61K 2800/87; A61K 2800/30; A61Q 11/00; A61C 19/063
See application file for complete search history.

(56) References Cited

U.S. PATENT DOCUMENTS

| | | |
|---|---|---|
| 5,876,744 A | 3/1999 | Della et al. |
| 9,320,699 B2 | 4/2016 | Porter et al. |
| 9,532,939 B2 | 1/2017 | Ripley et al. |
| 10,383,796 B2 | 8/2019 | Truitt |
| 2002/0028241 A1 | 3/2002 | Foreman et al. |
| 2004/0037789 A1 | 2/2004 | Moneuze |
| 2005/0142076 A1 | 6/2005 | Fukunaga et al. |
| 2007/0003502 A1 | 1/2007 | Tanabe et al. |
| 2007/0237726 A1* | 10/2007 | White ............... A61Q 11/00 433/84 |
| 2007/0298087 A1 | 12/2007 | Biegajski |
| 2009/0068122 A1 | 3/2009 | Pilch |
| 2011/0104081 A1 | 5/2011 | Scott |
| 2012/0014883 A1 | 1/2012 | Scott |
| 2012/0082630 A1 | 4/2012 | Haught |
| 2012/0202767 A1 | 8/2012 | Di |
| 2013/0017238 A1 | 1/2013 | Porter et al. |
| 2014/0242005 A1 | 8/2014 | Koumans |
| 2018/0333349 A1 | 11/2018 | Ansari et al. |
| 2019/0021966 A1 | 1/2019 | Jha et al. |
| 2020/0054667 A1 | 2/2020 | Mevorat Kaplan et al. |
| 2020/0297595 A1 | 9/2020 | Sagel et al. |
| 2020/0390677 A1 | 12/2020 | Strand |
| 2020/0390801 A1 | 12/2020 | Strand |

FOREIGN PATENT DOCUMENTS

| | | | |
|---|---|---|---|
| CN | 101415731 A | 4/2009 | |
| CN | 102125507 A | 7/2011 | |
| CN | 105213298 A | 1/2016 | |
| CN | 105434315 A | 3/2016 | |
| CN | 106963727 A | 7/2017 | |
| CN | 107432853 A | 12/2017 | |
| CN | 107468553 A | 12/2017 | |
| CN | 107496195 A | 12/2017 | |
| CN | 107536725 A | 1/2018 | |
| CN | 108324739 A | 7/2018 | |
| CN | 108888770 A | 11/2018 | |
| CN | 108939079 A | 12/2018 | |
| CN | 109010471 A | 12/2018 | |
| CN | 109528805 A | 3/2019 | |
| CN | 109820821 A | 5/2019 | |
| CN | 110123702 A | 8/2019 | |
| DE | 102017005168 A1 | 12/2018 | |
| EP | 2666517 A1 * | 11/2013 | ............. A61K 8/735 |
| EP | 2666517 A1 | 11/2013 | |
| EP | 3056195 A1 | 8/2016 | |
| JP | H08500578 A | 1/1996 | |
| JP | 2002029950 A | 1/2002 | |
| JP | 2004012747 A1 | 1/2004 | |
| JP | 2009274967 A | 11/2009 | |
| JP | 2010511053 A | 4/2010 | |
| JP | 2010138080 A | 6/2010 | |
| JP | 2012153677 A | 8/2012 | |
| JP | 2014501733 A | 1/2014 | |
| JP | 2015189708 A | 11/2015 | |
| JP | 2018002719 A | 1/2018 | |
| JP | 6519930 B2 * | 5/2019 | ............... A23L 5/00 |
| KR | 100794264 B1 | 1/2008 | |

(Continued)

OTHER PUBLICATIONS

International Search Report and Written Opinion; Application Ser. No. PCT/CN2019/091272; dated Mar. 12, 2020, 8 pages.

(Continued)

*Primary Examiner* — Snigdha Maewall
(74) *Attorney, Agent, or Firm* — Elizabeth A. Conklin

(57) ABSTRACT

Leave-on oral care compositions comprising a hyaluronic acid or a salt thereof having good spreadability and improved retention period are provided for promoting Gum Health of a user.

12 Claims, No Drawings

(56) References Cited

FOREIGN PATENT DOCUMENTS

| KR | 100805635 B1 | 2/2008 |
| WO | 2016112998 A1 | 7/2016 |
| WO | 2018212771 A1 | 11/2018 |
| WO | 2019025599 A1 | 2/2019 |

OTHER PUBLICATIONS

International Search Report and Written Opinion; Application Ser. No. PCT/CN2020/095595; dated Aug. 21, 2020, 7 pages.
All Office Actions; U.S. Appl. No. 16/899,882.
All Office Actions; U.S. Appl. No. 16/899,919.
Google patent search hyaluronic polyacrylic water, Retrieved from: https://patents.google.com/?q=hyaluronic+polyacrylic+water&oq=hyaluronic+polyacrylic+water, Retrieved on Jun. 29, 2021, 2 Pages.
Google scholar search hyaluronic polyacrylic mucoadhesive, Retrieved from: https://scholar.google.com/scholar?hl=en&as_sdt=0%2C5&q=hyaluronic+polyacrylic+mucoadhesive&btnG=, Retrieved on Jun. 29, 2021, 2 Pages.
Google search hyaluronic polyacrylic mucoadhesive, Retrieved from: https://www.google.com/search?q=hyaluronic_polyacrylic_mucoadhesive&rlz=1C1GCEA_enIN879IN879&oq=hyaluronic_polyacrylic_mucoadhesive&aqs=chrome..69i57.1423j0j15&sourceid=chrome&ie=UTF-8, Retrieved on Jun. 29, 2021, 2 Pages.
Google search polyvinylpyrrolidone mucoadhesive properties hyaluronic acid polyacrylic, Retrieved from: https://www.google.com/search?q=polyvinylpyrrolidone+mucoadhesive+properties+hyaluronic+acid+polyacrylic&rlz=1C1GCEA_enIN879IN879&oq=polyvinylpyrrolidone+mucoadhesive+properties+hyaluronic+acid+polyacrylic&aqs=chrome..69i57.505j0j15&sourceid=chrome&ie=UTF-8, Retrieved on Jun. 29, 2021, 2 Pages.
Roy et al., Polymers in Mucoadhesive Drug-Delivery Systems: A Brief Note, Designed monomers and polymers, vol. 12, Issue 6, Jan. 1, 2009, pp. 483-495.
Database GNPD [Online] Mintel; Anonymous: "Gengigel Oral Hygiene Range", XP055809999, Database accession No. 341172, Feb. 17, 2005.
Database GNPD [Online] Mintel; Anonymous: "Travel Kit", XP055729622, Database accession No. 6318883, Feb. 12, 2019.
International Search Report and Written Opinion; Application No. PCT/CN2020/095595; dated Sep. 13, 2021, 12 pages.
Dahiya P, Kamal R. Hyaluronic acid: A boon in periodontal therapy. North Am J Med Sci 2013;5:309-15. (Year: 2013).

* cited by examiner

LEAVE-ON ORAL CARE COMPOSITIONS

FIELD OF THE INVENTION

The present invention relates to oral care compositions comprising a hyaluronic acid or a salt thereof for promoting Gum Health of a user. In particular, such oral care compositions provide a leave-on formula which provide both good spreadability and retention property, so as to provide improved sensory experience and Gum Health benefit for the user.

BACKGROUND OF THE INVENTION

Users having gum problems have typically been limited to brushing teeth with toothpastes as a solution at home. This mechanism can help clean and control the plaque and bacteria and associated toxin challenge on the host. However, due to the limited residence time of brushing, 2 minutes, there is little time to repair, or even strengthen the host tissue. Accordingly, users expect a regimen that can be applied to the host tissue for a longer time and to repair, strengthen and rejuvenate the gum. To meet such users' expectation, a number of gel or ointment products that can be applied to the oral cavity have been developed to provide such benefits. For example, a user can apply a gel formulation product onto oral tissue, e.g. gum area and leave for some time before expectorating or alternatively without expectorating or rinsing off. Desirable products require sufficient substantivity and rheological properties to enable application to the oral cavity, to adhere to the oral tissue and to release the contained oral care benefits agents over an extended period of time. However, the viscosity should not be so high that the users can feel globular portions of the newly applied product that has not spread well over the tissue upon application. Unfortunately, few, if any, products can meet all users' needs. For example, some products have relatively low viscosity to provide good spreadability but are not sticky/tacky enough so hard to retain on the gum line or into the gum sulcus, while some other products are too sticky/tacky but are hard to spread.

Therefore, there is a need for a leave-on oral care composition which provides not only a good spreadability but also a good retention or adhesion property so that the composition can effectively release active ingredients to promote Gum Health.

SUMMARY OF THE INVENTION

A novel technology for formulating a leave-on oral care composition is developed by the inventors to meet at least some of the needs described above. Particularly, it is a surprising discovery that a leave-on oral care composition exhibiting a viscosity profile within in a specific range (such as the Viscosity Consistency Coefficient K between about 50 Pa·s to about 250 Pa·s as measured at 22° C. at a shear rate range of 0.1-10 $s^{-1}$) and/or a mucoadhesion property within a specific range (such as a Mucoadhesive Index of no less than about 0.6 FI %, as measured according to the Mucoadhesion Test Method described hereinafter) provides users with a desirable sensory feel. Particularly, such leave-on oral care compositions strike a good balance between different sensory aspects, such as spreadability, retention and/or adhesion.

It is advantageous that the leave-on oral care composition has an optimal viscosity so as to provide a good spreadability.

It is also advantageous that the leave-on oral care composition is not heavy, overly sticky/tacky and provide users enjoyable experiences, such as refreshing, safe, and effective feel.

It is further advantageous to provide users with a balanced feel between spreadability and tackiness.

It is still advantageous that the leave-on oral care composition containing a hyaluronic acid having optimal viscosity as well as optimal adhesion work can provide the users an improved Gum Health benefit, such as better wound healing benefit.

Without being bound by any theory, it is believed that the leave-on oral care composition of the present invention, which exhibits improved wound healing benefit and barrier function benefit, may in turn help to relieve gingival pain, promote gingival regeneration, accelerate repairing of mucosal/gingival damage and healing of gingival bleeding wound, and/or enhancing gingival immunity/resistance. The leave-on oral care composition may further help forming a protective film over lesion and irritation caused by ill-fitting dentures. The leave-on oral care composition may further help repairing or healing of gingival damage post root scaling/planning or gum grafts. The leave-on oral care composition may even further to help improve hydration to the mucosal and even help alleviate or relieve dry mouth.

It is yet advantageous to apply the leave-on oral care composition after brushing teeth, or as the last step of oral hygiene regimen. It is advantageous that the leave-on oral care composition is applied on the soft tissue of the oral cavity, leaving for more than 2 minutes, preferably more than 10 minutes, and without being rinsed off or expectorated.

It is further advantageous to apply the leave-on gel to the gum by using a delivery carrier, wherein the delivery carrier may comprise strip, film of material, dental tray, aligner, sponge material, applicator, or mixtures thereof.

In one aspect, the present invention is directed to an oral care composition comprising a hyaluronic acid or a salt thereof, wherein the composition has a Viscosity Consistency Coefficient K of from about 50 Pa·s to about 250 Pa·s as measured at 22° C. with a shear rate range of 0.1-10 $s^{-1}$. The oral care composition has a Mucoadhesion Index of no less than 0.6 FI %, as measured according to the Mucoadhesion Test Method described therein. Preferably, the oral care composition is a leave-on composition. Preferably, the hyaluronic acid has a weight average molecular weight from about 900,000 Daltons to about 5,000,000 Daltons, preferably from about 900,000 Daltons to about 2,000,000 Daltons. More preferably, the hyaluronic acid is present in the amount of from about 0.1% to about 5.0%, more preferably from about 0.2% to about 0.8%, by weight of the composition.

In another aspect, the above-mentioned oral care composition further comprises from about 0.1% to about 10%, preferably from about 0.5% to about 5%, more preferably from about 1% to about 4%, by weight of the composition, of polyacrylic acid. Preferably, the above-mentioned oral care composition further comprises from about 0.1% to about 10%, preferably from about 0.5% to about 5%, more preferably from about 1% to about 4%, by weight of the composition, of an additional polymer selected from natural gum, linear sulfated polysaccharide, anionic cellulose, non-ionic cellulose derivative, polyvinyl pyrrolidine, and combinations thereof.

In another aspect of the present invention, the above-mentioned oral care composition further comprises from about 30% to about 85%, preferably from more than about 40% to about 80%, preferably from about 45% to about 75%, by weight of the composition, of total water content. Preferably, the above-mentioned oral care composition is substantially free of abrasives, preferably essentially free of abrasives.

In still another aspect of the present invention, there is provided a method of improving Gum Health of a subject using the oral care composition as defined therein, comprising the step of applying the oral care composition onto the intraoral tissue of the subject, on which the oral care composition is left without removal for a duration of time from 1 minute to 1000 minutes, preferably from 2 minutes to 200 minutes; optionally the applying step can be conducted as the last step of an oral hygiene regimen.

In still another aspect of the present invention, there is provided a method of improving Gum Health of a subject, comprising at least two steps: (a) brushing teeth with a toothpaste, preferably an antibacterial toothpaste, more preferably a stannous containing toothpaste, and even more preferably a toothpaste containing a stannous ion source and an amino acid; and subsequently, preferably immediately followed by (b) applying the oral care composition as defined herein onto the intraoral tissue of a subject, preferably applying along the gingival margin, sulcus or pockets, on which the oral care composition is left for a duration of time from 1 minute to 1000 minutes.

In yet still another aspect of the present invention, there is provided a kit comprising an oral care composition of the present invention and a delivery carrier, wherein the delivery carrier comprises strip, film of material, dental tray, aligner, sponge material, applicator, or mixtures thereof. In a preferred example, the kit comprises an oral care composition of the present invention and an applicator having a handle and a head. There is also provided a kit comprising a toothpaste and the oral care composition of the present invention. In one example, the kit comprises an antibacterial toothpaste and the oral care composition of the present invention. Preferably, the toothpaste is a stannous-containing toothpaste, more preferably is a toothpaste comprising a stannous ion source and an amino acid. Preferably, the toothpaste and the oral care composition are sequentially applied to improve Gum Health.

These and other features of the present invention will become apparent to one skilled in the art upon review of the following detailed description when taken in conjunction with the appended claims.

DETAILED DESCRIPTION OF THE INVENTION

Definitions

As used herein, the articles including "a" and "an" when used in a claim, are understood to mean one or more of what is claimed or described.

The term "comprising" as used herein means that steps and ingredients other than those specifically mentioned can be added. This term encompasses the terms "consisting of" and "consisting essentially of." The compositions of the present invention can comprise, consist of, and consist essentially of the essential elements and limitations of the invention described herein, as well as any of the additional or optional ingredients, components, steps, or limitations described herein.

As used herein, the words "preferred", "preferably" and variants refer to embodiments of the invention that afford certain benefits, under certain circumstances. However, other embodiments may also be preferred, under the same or other circumstances. Furthermore, the recitation of one or more preferred embodiments does not imply that other embodiments are not useful; and is not intended to exclude other embodiments from the scope of the invention.

The term "gingival gel" or "gum gel" as used herein means a product or a composition is in a form of gel which intent to primarily applied to the gum of a subject, preferably more than 50% of the product or composition is applied to the gum.

As used herein, "leave-on" means a product or a composition is adopted or applied onto a surface for a certain amount of time, e.g. more than one minute, preferably more than two minutes. Preferably, a "leave-on" gel means a gel product or composition which is intent not to be rinsed off or expectorated.

The term "Gum Care" means those benefits aiming to alleviate one or more symptoms of the earlier stage of gum disease (i.e., gingivitis), which includes: relief of red, swollen, or tender gums; and/or stem gum bleeding.

The term "Gum Health" as used herein refers to inherent or promoted benefits of an oral care composition to provide "Gum Care" benefits that include at least improve gingival wound healing, as well as, providing additional improve reduction of bacterial activity to mitigate the harmful effects of bacteria as it relates to gum disease, including gingivitis, periodontitis or both.

The term "promoting" as used herein means to promote and/or enhance the Gum Health benefits associated with using the oral care compositions of the present invention in the oral cavity.

The term "substantially free" as used herein refers to the presence of no more than 0.05%, preferably no more than 0.01%, and more preferably no more than 0.001%, of an indicated material in a composition, by total weight of such composition.

The term "essentially free" as used herein means that the indicated material is not deliberately added to the composition, or preferably not present at analytically detectable levels. It is meant to include compositions whereby the indicated material is present only as an impurity of one of the other materials deliberately added.

The term "oral hygiene regimen' or "regimen" can be for the use of two or more separate and distinct treatment steps for oral health. e.g. toothpaste, mouth rinse, floss, toothpicks, spray, water irrigator, massager.

The term "total water content" as used herein means both free water and water that is bound by other ingredients in the oral care composition.

All percentages, parts and ratios are based upon the total weight of the compositions of the present invention, unless otherwise specified. All such weights as they pertain to listed ingredients are based on the active level and, therefore do not include solvents or by-products that may be included in commercially available materials, unless otherwise specified.

All measurements referred to herein are made at 25° C. (i.e., room temperature) unless otherwise specified.

Oral Care Compositions

The oral care composition described in the present invention is configured for applying on the gingival tissue, as well as other soft tissue (e.g. buccal mucosa) inside the oral cavity of a subject. It has been surprisingly discovered that an oral care composition having both an optimal viscosity and a good adhesion and retention efficacy provides a better sensory benefit to the users, and also is particularly useful for promoting Gum Health benefits to users.

The oral care composition described therein is a leave-on composition. The leave-on composition is applied to the gingival tissue, e.g. gumline area, and left on for more than 2 minutes, preferably more than 10 minutes, more preferably more than 30 minutes and more preferably 60 minutes or longer. Preferably, the leave-on composition is applied to the gingival tissue as the last step of oral hygiene regimen. For example, the leave-on composition of the present invention is applied after brushing teeth, and optionally after using mouth rinse and/or floss.

In one aspect, the present invention is directed to an oral care composition which is in a gel form. It is desirable to have a gel for use in the present invention that enables easy application, thin layer formation and evenly spread into gingival sulcus/pockets and along gingival gum line. The oral care composition has a Viscosity Consistency Coefficient K of about 50 Pa·s to about 250 Pa·s, as measured by the Rheological Test method described herein. Preferably, the oral care composition has a Viscosity Consistency Coefficient K of about 50 Pa·s to about 200 Pa·s, preferably from about 50 Pa·s to about 150 Pa·s, more preferably from about 50 Pa·s to about 120 Pa·s, even more preferably from 50 Pa·s to 100 Pa·s. This optimal viscosity profile range provides better sensory experience of spreadability for a user. If a product is too viscous, it would be hard for a user to spread it evenly onto gingival tissue. If the product has a too low viscosity, it is runny and hard to be retained on appropriate area by finger or applicator.

In one aspect, the oral care composition of present invention has a desirable mucoadhesion property. Mucoadhesion can be defined as adhesive interaction between two surfaces where one is at least mucosa for a given period through interfacial forces with a consequent decreased in the surface energy. Mucoadhesion polymers for oral care application should ideally (1) easily retain hydrophilic and lipophilic active ingredients and not hinder their release; (2) promote active ingredient penetration and absorption, (3) adhere as quickly as possible to biological substrate and be retained for a period of time, (4) be safe, (5) be cost effective and (6) provide user acceptable application.

The oral care composition of present invention has a Mucoadhesion Index in the range of not less than 0.6 FI %, as measured by the Mucoadhesion Test Method described herein. Preferably, the oral care composition has a Mucoadhesion Index of no less than about 0.8 FI %, more preferably no less than about 1.0 FI %. For instance, the oral care composition may have a Mucoadhesion Index of no less than about 1.2 FI %, or no less than about 1.3 FI %, or no less than about 1.5 FI %, or no less than about 1.8 FI %, or no less than about 2.0 FI %. Preferably, the oral care composition has a Mucoadhesion Index of less than about 20 FI %, preferably less than about 15 FI %, more preferably less than about 10 FI %.

Hyaluronic Acid and Salts

The oral care composition of the present invention comprises a hyaluronic acid or a salt thereof. Hyaluronic acid is a polysaccharide present in the connective tissue of vertebrates, a polymer of glucuronic acid and n-acetyglucosylamine, and is a member of glucosamine family with a high molecular weight. Hyaluronic acid (Hyaluronan) is an indispensable component of intact, healthy gingiva, and oral mucosal tissue. It has many properties that make it a potentially ideal molecule for assisting wound healing by inducing early granulation tissue formation, inhibiting inflammation, promoting epithelial turnover and also connective tissue angiogenesis. Preferably, the hyaluronic acid used in the present invention has a weight average molecular weight (M.W.) of from about 900,000 Daltons to about 5,000,000 Daltons, preferably from about 900,000 Daltons to about 3,000,000 Daltons; more preferably from about 900,000 Daltons to about 2,000,000 Daltons. The molecular weight of the hyaluronic acid can be measured using Gel Electrophoresis method. The hyaluronic acid of the present invention is present in the amount of from about 0.1% to about 5% by weight of the composition. Preferably, the hyaluronic acid is present in the amount of from about 0.2% to about 2%, more preferably from about 0.2% to about 0.8%, by weight of the composition. For example, the hyaluronic acid is present in the amount of about 0.2%, or about 0.3%, or about 0.4%, or about 0.5%, or about 0.6%, or about 0.7%, or about 0.8%, or about 0.9%, or about 1.0%, by weight of the composition. Any salt of the hyaluronic acid suitable for oral care product can be used in the present invention. Preferably, the hyaluronate salt may be sodium hyaluronate.

Mucoadhesive Polymer

The oral care composition of the present invention comprises polyacrylic acid as a mucoadhesive polymer. Polyacrylic acid (PAA) polymer is a generic term for the synthetic high molecular weight polymers of acrylic acid. These may be homopolymers of acrylic acid, crosslinked with an allyl ether pentaerythritol, allyl ether of sucrose or allyl ether of propylene. And, in a water solution at neutral pH, PAA is an anionic polymer, i.e. many of the side chains of PAA will lose their protons and acquire a negative charge. This makes PAAs polyelectrolytes, with the ability to absorb and retain water and swell to many times their original volume. Polyacrylic acid is also called carbomer as tradename. For example, Carbopol®-type polymers, such as Carbopol®, Pemulen® and Noveon®, are polymers of acrylic acid, crosslinked with polyalkenyl ethers or divinyl glycol. Carbomer commercial codes, e.g. 940™, indicate the molecular weight and the specific components of the polymer.

Preferably, the polyacrylic acid used in the invention is present in the amount of from about 0.1% to about 10% by weight of the oral care composition. For example, the polyacrylic acid is present in the amount of about 0.2% to about 5%, or about 0.5% to about 8%, or about 1.0% to about 5%, by weight of the oral care composition.

Additional Polymer

The oral care composition of the present invention may comprise an additional polymer. Preferably the oral care composition comprises from about 0.1% to about 10%, preferably from about 0.5% to about 6%, more preferably from about 1% to about 5%, yet still more preferably from about 1.3% to about 2.6%, by weight of the composition, of the additional polymer. The additional polymer is selected from natural gum, linear sulfated polysaccharide, anionic cellulose, nonionic cellulose derivative, polyvinyl pyrrolidine, polymers comprising at least a polycarboxylated ethylene backbone, and combinations thereof.

Preferably, a natural gum is selected from the group consisting of gum karaya, gum arabic (also known as acacia gum), gum tragacanth, xanthan gum, and combination thereof. More preferably, the natural gum is xanthan gum. Xanthan gum is a polysaccharide secreted by the bacterium *Xanthomonas camestris*. Generally, xanthan gum is composed of a penta-saccharide repeat units, comprising glucose, mannose, and glucuronic acid in a molar ratio of 2:2:1, respectively. The chemical formula (of the monomer) is $C_{35}H_{49}O_{29}$. In one example, the xanthan gum is from CP Kelco Inc (Okmulgee, US).

Preferably, the linear sulfated polysaccharide is a carrageenan. Examples of carrageenan include Kappa-carrageenan, Iota-carrageenan, Lambda-carrageenan, and combinations thereof. In one example, the linear sulfated polysaccharide is Iota-carrageenan.

Preferably, the anionic cellulose is a carboxymethyl cellulose ("CMC"). In one example, the CMC is prepared from cellulose by treatment with alkali and monochloroacetic acid or its sodium salt. Different varieties are commercially characterized by viscosity. One commercially available example is Aqualon™ branded CMC from Ashland Special Ingredients (e.g., Aqualon™ 7H3SF; Aqualon™ 9 M3SF Aqualon™ TM9A; Aqualon™ TM12A).

Preferably, the nonionic cellulose or derivative thereof has a weight average molecular weight range of about 50,000 Daltons to about 1,300,000 Daltons, and preferably an average degree of polymerization from 300 to 4,800. More preferably, the nonionic cellulose or derivative thereof is hydroxyethyl cellulose ("HEC"). In other examples, the nonionic cellulose may be hydroxypropyl cellulose or hydroxymethyl cellulose.

Preferably, the polymer comprising at least a polycarboxylated ethylene backbone is selected from the group consisting of: co-polymers of maleic anhydride with methyl vinyl ether having a weight average molecular weight of from about 30,000 Daltons to about 1,000,000 Daltons; and co-polymers of maleic acid and acrylic acid or methacrylic.

In an example, the GANTREZ™ series of polymers are co-polymers of maleic anhydride with methyl vinyl ether having a weight average molecular weight (M.W.) of about 30,000 Daltons to about 1,000,000 Daltons. These co-polymers are available for example as GANTREZ™ AN139 (M.W. 500,000 Daltons), AN119 (M.W. 250,000 Daltons) and S-97 Pharmaceutical Grade (M.W. 70,000 Daltons), from Ashland Chemicals (Kentucky, USA).

In another example, the ACUSOL™ and the SOKALAN series of polymers include homopolymers of acrylic acid and copolymers of maleic acid and acrylic acid or methacrylic. Examples are 0:1000 to 1000:0 copolymers of maleic acid with acrylic acid having a weight average molecular weight (M.W.) of about 2,000 to about 1,000,000 Daltons. These copolymers are commercially available as ACUSOL™ 445 and 445N, ACUSOL™ 531, ACUSOL™ 463, ACUSOL™ 448, ACUSOL™ 460, ACUSOL™ 465, ACUSOL™ 497, ACUSOL™ 490 from Dow Chemicals (Michigan, USA) and as Sokalan® CP 5, Sokalan® CP 7, Sokalan® CP 45, and Sokalan® CP 12 S from BASF (New Jersey, USA).

In some examples, the ratio of the mucoadhesive polymer and the additional polymer in the oral care composition of the present invention is from about 5:1 to about 1:5, preferably from about 3:1 to about 1:3. For example, the ratio of the polyacrylic acid and the additional polymer in the present oral care composition, by weight, is about 4:1, or about 3:1, or about 2:1, or about 1.5:1, or about 1:1, or about 1:1.5, or about 1:2, or about 1:2.5, or about 1:3, or about 1:4, or about 1:5.

Water

The term "orally acceptable carrier" as used herein means a liquid or semi-solid vehicle such as a paste or a gel for containing the active ingredients of the present invention and delivering them to the oral cavity. Water is commonly used as a carrier material in oral compositions due to its many benefits. For example, water is useful as a processing aid, is benign to the oral cavity and assists in quick foaming of toothpastes. Water may be added as an ingredient in its own or it may be present as a carrier in other common raw materials such as, for example, sorbitol and sodium lauryl sulphate. The term total water content as used herein means the total amount of water present in the oral care composition, whether added separately or as a solvent or carrier for other raw materials but excluding that which may be present as water of crystallization in certain inorganic salts.

The oral care composition of the present invention comprises at least about 30% of a total water content. Preferably, the oral care composition comprises from more than about 35% to about 85% of a total water content. In other embodiments, the compositions include from about 40% to about 80%, alternatively from about 45% to about 75%, alternatively from about 50% to about 70%, alternatively from about 50% to about 60%, alternatively from about 45% to about 55%, alternatively from about 55% to about 65%, alternatively from about 65% to about 75%, alternatively combinations thereof, of a total water content.

Free of Abrasives

Preferably the oral care composition of the present invention is substantially free of abrasives. The term "abrasive", for the purpose of present invention, includes calcium-containing abrasives and silica abrasives. The calcium-containing abrasives may be selected from the group consisting of calcium carbonate, dicalcium phosphate, tricalcium phosphate, calcium orthophosphate, calcium metaphosphate, calcium polyphosphate, calcium oxyapatite, sodium carbonate, and combinations thereof. In one embodiment where the calcium-containing abrasive is calcium carbonate, the calcium carbonate can be selected from the group consisting of fine ground natural chalk, ground calcium carbonate, precipitated calcium carbonate, and combinations thereof. The silica abrasives may generally have an average particle size ranging from 0.1 to 30 µm, and preferably from 5 to 15 µm. The silica abrasives can be precipitated silica or silica gels such as the silica xerogels marketed under the trade name "Syloid" by the W.R. Grace & Company, Davison Chemical Division and precipitated silica materials such as those marketed by the J. M. Huber Corporation under the trade name, Zeodent®, particularly the silicas carrying the designation Zeodent® 119, Zeodent® 118, Zeodent® 109 and Zeodent® 129.

Preferably, the oral care composition of the present invention contains low levels of abrasives. For example, the oral care composition may comprise from 0% to about 5% by weight of the composition, of abrasives, alternatively from 0% to about 3%, alternatively from 0% to about 2%, alternatively from 0% to about 1%, alternatively less than about 3%, or less than about 2%, or less than about 1%, or less than about 0.5%, by weight of the composition. Preferably, the composition is substantially free of the abrasives, more preferably free of the abrasives.

Humectants

The oral care compositions herein may contain humectants. The humectants serve to keep the oral care composition from hardening upon exposure to air, to give a moist feel to the mouth, and, for particular humectants, to impart a desirable sweetness of flavor.

Suitable humectants for the present invention include edible polyhydric alcohols such as glycerin, sorbitol, xylitol, erythritol, butylene glycol, polyethylene glycol, propylene glycol, and combinations thereof. In one embodiment, the humectant is selected from sorbitol, glycerin, and combinations thereof. In another embodiment, the humectant is glycerin. In yet another embodiment, the humectant is sorbitol. In one embodiment, the oral care composition comprises from about 1% to less than about 50% of humectants by weight of the composition, preferably from about 10% to about 40%. In yet another embodiment, the oral care composition contains from about 15% to about 30% of glycerin by weight of the oral care composition.

In one example, the oral care composition of the present invention is substantially free of ethanol, preferably essentially free of ethanol. The ethanol is not desirable, in some cases, as it may cause irritating feeling to the users.

Flavorant

The oral care compositions herein may include from about 0.001% to about 5%, alternatively from about 0.01% to about 4%, alternatively from about 0.1% to about 3%, alternatively from about 0.5% to about 2%, alternatively combination thereof, of a flavorant composition by weight of the oral care composition. The term flavorant composition is used in the broadest sense to include flavor ingredients, or sensates, or sensate agents, or combinations thereof. Flavor ingredients may include those described in U.S. Publication No. 2012/0082630A1 at paragraph 39; and sensates and sensate ingredients may include those described at paragraphs 40-45, incorporated herein by reference.

Examples of flavor compositions or flavor ingredients include: mint oils, wintergreen, clove bud oil, cassia, sage, parsley oil, marjoram, lemon, orange, propenyl guaethol, heliotropine, 4-cis-heptenal, diacetyl, methyl-p-tert-butyl phenyl acetate, methyl salicylate, ethyl salicylate, 1-menthyl acetate, oxanone, a-irisone, methyl cinnamate, ethyl cinnamate, butyl cinnamate, ethyl butyrate, ethyl acetate, methyl anthranilate, iso-amyl acetate, iso-amyl butyrate, allyl caproate, eugenol, eucalyptol, thymol, cinnamic alcohol, octanol, octanal, decanol, decanal, phenylethyl alcohol, benzyl alcohol, a-terpineol, linalool, limonene, citral, neral, geranial, geraniol nerol, maltol, ethyl maltol, anethole, dihydroanethole, carvone, menthone, beta-damascenone, ionone, gamma-decalactone, gamma-nonalactone, y-undecalactone, or combinations thereof. Generally suitable flavor ingredients are chemicals with structural features and functional groups that are less prone to redox reactions. These include derivatives of flavor ingredients that are saturated or contain stable aromatic rings or ester groups.

Sensates such as cooling, warming, and tingling agents are useful to deliver signals to the users. The most well-known cooling agent is menthol, particularly 1-menthol, which is found naturally in peppermint oil. Among synthetic cooling agents, many are derivatives of or are structurally related to menthol, i.e., containing the cyclohexane moiety, and derivatized with functional groups including carboxamide, ketal, ester, ether and alcohol. Examples include the p-menthanecarboxamide compounds such as N-ethyl-p-menthan-3-carboxamide (known commercially as "WS-3"). An example of a synthetic carboxamide cooling agent that is structurally unrelated to menthol is N,2,3-trimethyl-2-isopropylbutanamide. Additional exemplary synthetic cooling agents include alcohol derivatives such as 3-1-menthoxypropane-1,2-diol, isopulegol, p-menthane-3,8-diol; menthone glycerine acetal (known commercially as "MGA"); menthyl esters such as menthyl acetate, menthyl acetoacetate, menthyl lactate, and monomenthyl succinate.

Additional agents that are structurally unrelated to menthol but have been reported to have a similar physiological cooling effect include alpha-keto enamine derivatives described in U.S. Pat. No. 6,592,884, including 3-methyl-2-(1-pyrrolidinyl)-2-cyclopenten-1-one (3-MPC), 5-methyl-2-(1-pyrrolidinyl)-2-cyclopenten-1-one (5-MPC); 2,5-dimethyl-4-(1-pyrrolidinyl)-3(2H)-furanone (DMPF); icilin (also known as AG-3-5, chemical name 142-hydroxyphenyll-4-[2-nitrophenyll-1,2,3,6-tetrahydropyrimidine-2-one).

Some examples of warming agents include ethanol; nicotinate esters, such as benzyl nicotinate; polyhydric alcohols; nonanoyl vanillyl amide; nonanoic acid vanillyl ether; vanillyl alcohol alkyl ether derivatives such as vanillyl ethyl ether, vanillyl butyl ether, vanillyl pentyl ether, and vanillyl hexyl ether; isovanillyl alcohol alkyl ethers; ethylvanillyl alcohol alkyl ethers; veratryl alcohol derivatives; substituted benzyl alcohol derivatives; substituted benzyl alcohol alkyl ethers; vanillin propylene glycol acetal; ethylvanillin propylene glycol acetal; ginger extract; ginger oil; gingerol; zingerone; or combinations thereof.

Examples of some tingling agents include capsaicin; homocapsaicin, jambu oleoresin, zanthoxylum peperitum, saanshool-I, saanshool II, sanshoamide, piperine, piperidine, spilanthol, 4-(1-methoxymethyl)-2-phenyl-1,3-dioxolane, or combinations thereof.

The oral care compositions herein can further include herbal ingredients such as extracts of chamomile, oak bark, melissa, rosemary and *salvia*. These, and some of the herb-derived flavoring components can be included at levels just sufficient to provide a contribution to the flavor or they can be added at higher levels, such as 1% or more, in order to provide a greater therapeutic effect.

Preservatives

The oral care composition of the present invention may comprise preservatives. The preservatives may be benzyl alcohol, phenoxyethanol, sorbitan caprylate (Velsan SC®), 1-2 hexanediol & caprylyl glycol (Symdiol 68®), parabens and or combinations. The paraben may comprise methyl paraben or propyl paraben or combination thereof. Levels of benzyl alcohol or phenoxyethanol may be present at the amount of from greater than about 0.10% to about 0.40%, preferably about 0.12% to about 0.30%, more preferably about 0.15% to about 0.23%, alternatively from about 0.18% to about 0.22%, alternatively from about 0.19% to about 0.21%, alternatively about 0.20%, by weight of the composition. The levels of Velsan C® maybe present at the amount of from about 0.10% to about 0.50%, preferably from about 0.20% to about 0.40%, more preferably alternatively from about 0.25% to about 0.30%. The level of Symdiol 68® maybe present from about 0.10% to about 0.80%, preferably from about 0.10% to about 0.50% and more preferably about 0.20% to about 0.30%. Levels of paraben may be present at the amount of about 0.01% to about 0.11%, preferably about 0.02% to about 0.10%, more preferably about 0.03% to about 0.09%, by weight of the composition. In one embodiment, the composition comprises from about 0.005% to about 0.1%, preferably from about 0.01% to about 0.08%, alternatively from about 0.01% to about 0.05%, of propyl paraben by weight of the composition. In another embodiment, the composition comprises from about 0.01% to about 0.1%, preferably from about 0.02% to about 0.07%, alternatively from about 0.03% to about 0.05%, of methyl paraben by weight of the composition.

In yet another embodiment, the paraben comprises a combination of methyl paraben and propyl paraben, wherein there is a greater weight ratio of methyl paraben to propyl paraben. In yet still another embodiment, the paraben is methyl paraben and propyl paraben, wherein the weight ratio of methyl paraben to propyl paraben is from about 5:3 to about 30:3, preferably greater than about 5:3 to about 20:3, more preferably from about 6:3 to about 15:3.

In one embodiment, the oral care compositions of the present invention are substantially free of triclosan (i.e., 5-chloro-2-(2,4-dichlorophenoxy)phenol), preferably free of triclosan.

Sweetener

The oral care compositions herein may include a sweetening agent. These include sweeteners such as saccharin, dextrose, sucrose, lactose, xylitol, maltose, levulose, aspartame, sodium cyclamate, D-tryptophan, dihydrochalcones, acesulfame, sucralose, neotame, and mixtures thereof. Sweetening agents are generally used in oral care compositions at levels of from about 0.005% to about 5%, alternatively about 0.01% to about 1%, by weight of the composition, alternatively from about 0.1% to about 0.5%, alternatively combinations thereof.

Coloring Agents

The oral care compositions herein may include a coloring agent (i.e., pigments, dyes and opacifiers). The coloring agent may be in the form of an aqueous solution, preferably 1% coloring agent in a solution of water. Titanium dioxide may also be added to the present oral care composition. Titanium dioxide is a white powder which adds opacity to the oral care compositions. Titanium dioxide generally comprises from about 0.25% to about 5%, by weight of the composition. It will be appreciated that selected components for the compositions must be chemically and physically compatible with one another.

Anti-Calculus Agent

The oral care compositions may include an effective amount of an anti-calculus agent, which in one embodiment may be present from about 0.05% to about 50%, alternatively from about 0.75% to about 25%, alternatively from about 0.1% to about 15%. Non-limiting examples include those described in U.S. Publication No. 2011/0104081A1 at paragraph 64, and those described in U.S. Publication No. 2012/0014883A1 at paragraphs 63 to 68, as well as the references cited therein. One example is a pyrophosphate salt as a source of pyrophosphate ion. In one embodiment, the composition comprises tetrasodium pyrophosphate (TSPP) or disodium pyrophosphate or combinations thereof, preferably from about 0.01% to about 2%, more preferably from about 0.1% to about 1% of the pyrophosphate salt by weight of the composition. Without wishing to be bound by theory, TSPP may provide not only calcium chelating thereby mitigating plaque formation, but also may also provide the additional benefit of monofluorophosphate stabilization (in those formulations containing monofluorophosphate).

Other Ingredients

The present oral care composition may comprise other oral care active. For example, the oral care composition may comprise vitamins selected from Vitamin C, Vitamin E, Vitamin B5, and the combinations thereof. Herein the term "Vitamin" means said vitamin and all derivatives thereof. The ingredients may provide additional benefits to the oral care composition. The use of extracellular antioxidants, e.g. ascorbate or α-tocopherol, as chain breaking or radical scavenging antioxidants, helps control and modulate the intracellular reactive oxygen species (ROS) that can cause host-tissue damage. The use of dexpanthenol can improve epithelialization and induce the proliferation phase in the wound healing of damaged tissue.

In some embodiments, the oral care composition may comprise from about 0.1% to about 10%, preferably from about 0.5% to about 8%, or from about 0.5% to about 5%, by weight of the composition, of vitamins selected from Vitamin C, Vitamin E, Vitamin B5, or the combinations thereof. The vitamins described in the present invention means said vitamins and all derivatives thereof.

The present oral care composition may further comprise the usual and conventional ancillary components such as surfactants, anti-microbial agents, fluoride ions, and other ingredients that are known to one skilled in the art. It will be appreciated that selected components for the oral care compositions must be chemically and physically compatible with one another.

Method of Use

The present invention also relates to methods for treating the oral cavity comprising applying to the intraoral tissue (e.g. oral mucosa, gingiva) of the oral cavity of a subject, particularly the gum tissue, leaving on for more than 2 minute, preferably more than 10 minutes, more preferably more than 30 minutes, or more than 60 minutes or longer. The method of use herein comprises contacting a subject's oral mucosa (e.g. gingival margin or gingival sulcus/pockets) with the oral care composition according to the present invention.

The present invention further relates to a method of improving Gum Health of a subject using the oral care composition described herein comprising the step of applying the oral care composition onto the intraoral tissue of a subject, preferably applying along the gingival margin or sulcus at least once a day, preferably at least twice a day, more preferably every time immediately after brushing teeth. The term "immediately" herein means within 1 hour, preferably within 30 minutes, more preferably within 15 minutes, alternatively within 10 minutes. Preferably, the oral care composition can be applied onto the intraoral tissue of a subject by using an applicator, which applicator has a handle and a head, to spread the oral care composition along the gingival margin or sulcus of the subject. Preferably, the oral care composition is applied on the head of the applicator before being applied onto the intraoral tissue.

The present invention further relates to a method of improving Gum Health of a subject, comprising at least two steps: (a) brushing teeth with an antibacterial toothpaste, preferably a stannous containing toothpaste, and immediately followed by (b) applying the oral are composition as defined herein onto the intraoral tissue of a subject, preferably applying along the gingival margin, sulcus or pockets.

Test Methods

Test 1: Rheological Test Method

A Rheological Test Method is described for assessing viscosity profile (and ran according to manufacturing instructions). The viscosity profiles are tested on a TA AR2000 rheometer (available from TA Instruments, New Castle, United States) by using Dentifrice Macro Rheology Test procedure. The geometry used is 40 mm steel parallel plate with solvent trap. Dentifrice is placed on the Peltier Plate of AR2000 rheometer and the Gap setting is 1000 micron. Dentifrice Macro Rheology Test consists of stress sweep oscillation, frequency sweep oscillation and steady state flow tests. The key parameter settings are listed: (a) Stress sweep step: Oscillation Stress (Pa): 0.01-500; (b) Frequency (Hz): 1.0; (c) Frequency sweep step: Frequency (Hz): 0.1-10, and Controlled Oscillation Stress (Pa): 1.5; (d) Steady state flow step 1: Shear rate ($s^{-1}$): 0.01-100; and (e) Steady state flow step 2: Shear rate ($s^{-1}$): 100-0.01.

Shear flow test is a viscosity testing mode to measure the viscosity at different shear rates. Steady state flow test is a flow in which the velocity at every point does not vary with time. The three main parameters in this test are viscosity, shear rate and shear stress. Power Law Model is a well-known model used to characterize the relationship between viscosity or shear stress and shear rate over the range of shear rates where shear thinning occurs in a Non-Newtonian fluid. It quantifies overall viscosity range and degree of deviation from Newtonian behavior. The Power Law Model is described as $\eta=K\gamma^{n-1}$, wherein $\eta$=viscosity and $\gamma$=shear rate. K is known as the Viscosity Consistency Coefficient, describing the overall range of viscosities across the part of the flow curve that is being modelled. The exponent "n" is known as the rate index. K and η can be determined by Power Law Model fitting. Based upon rate index n, the Power Law Model describes three basic types of flow:

| n = 1 | Newtonian behavior |
| n < 1 | Shear thinning (or Pseudoplastic) |
| n > 1 | Shear thickening |

The viscosity profiles of the composition herein are represented by the Viscosity Consistency Coefficient K (Pa·s) determined by Power Law Model fitting with the shear rate range of 0.1-10 $s^{-1}$.

Test 2: Mucoadhesion Test Method

Mucoadhesion Test Method is provided. Test samples are labeled with Fluorescein isothiocyanate (FITC) at room temperature for 1 hour. The resulting solutions are dialyzed in phosphate buffered saline (PBS) for 48 h in order to remove the free FITC molecules. The silica wafers are treated with a mixture of ethanol/(3-Aminopropyl)triethoxysilane (APTES)/ammonia solution (20:4:1, v/v/v) for 8 hours and are then rinsed with ethanol and water, and dried to obtain the amine-functionalized silica wafers ($NH_2$—SW). $NH_2$—SW are incubated in mucin solution for 8 hours at room temperature. The mucin modified silica wafers are incubated with test sample in a PBS buffer in a shaker at 37° C. for 12 hours followed by rinsing with deionized water. The fluorescence images of the mucin modified silica wafers are taken by a fluorescence microscopy, and used for measurement of Fluorescent Intensity (FI) in ImageJ software (National Institutes of Health, USA, (https://imagej.nih.gov/ij/)). The Fluorescent Intensity Percentage ("FI %"), which is used to describe the "Mucoadhesion Index", is the fluorescent pixels relative to total pixels in a normalized image field. Therefore, a first test sample having a higher FI % has stronger mucoadhesion compared to a second test sample having a lower FI %.

Test 3: Adhesiveness Test Method

The adhesiveness of samples is tested using Texture Analyser (TA Plus/30), Stable Micro System (Surrey, UK). The procedure is described as below:
1. Sample preparation: pipe out of gel or ointment sample from package as the amount of '0.03±0.005 g' to the test plate.
2. Make TA sequence to enable the instrument action: the probe is compressed into each sample, follow the determined programmed sequence (speed of 10 mm/sec, force of 5 g for stage 2; speed of 1 mm/sec, Force of 200 g for stage 4, and time is 1 sec for stage 5).
3. Instrument & accessory setting:
   3.1 Try the test with available probe options: metal round plate
   3.2 TA setting as 'compression'
4. All analyses should be performed on 5 replicates.
5. measurement: Adhesiveness: the work necessary to overcome the attractive forces between the surface of the sample and the surface of the probe.
6. Data calculation: Leverage programmed TTA data analysis macro (e.g. Force 5 g).

The adhesiveness values (unit: gf*sec) describes the energy necessary to overcome the attractive forces between the surface of the sample and the surface of the probe.

EXAMPLES

The following examples and descriptions further clarify embodiments within the scope of the present invention. These examples are given solely for the purpose of illustration and are not to be construed as limitations of the present invention as many variations thereof are possible without departing from the spirit and scope.

Example A: Examples 1 to 5

Examples 1 to 5 are gel compositions according to the present invention, which are shown in Table 1 below with amounts of components in wt %. They may be suitably prepared by conventional methods chosen by the formulator.

TABLE 1

Gel Composition Examples 1 to 5

| Ingredients | Amount (wt %) | | | | |
| --- | --- | --- | --- | --- | --- |
|  | Ex. 1 | Ex. 2 | Ex. 3 | Ex. 4 | Ex. 5 |
| Glycerin | 20 | 20 | 20 | 20 | 20 |
| Propyl Paraben | 0.03 | 0.03 | 0.03 | 0.03 | 0.03 |
| Xylitol | 2 | 2 | 2 | 2 | 2 |
| Sodium Saccharin | 0.1 | 0.1 | 0.1 | 0.1 | 0.1 |
| Sodium Hydroxide (50%) | 0.9 | 0.9 | 0.9 | 0.9 | 0.9 |
| PEG 300 | 0.5 | 0.5 | 0.5 | 0.5 | 0.5 |
| Carbomer | 1.5 | 2.5 | 1.5 | 3.0 | — |
| Carrageenan | — | 1.0 | — | — | — |
| HEC | — | — | 1.5 | — | 3.0 |
| Gantrez | — | — | — | 2.0 | 2.0 |
| PVPK90 | 1.5 | — | — | — | — |
| Sodium Hyaluronate* | 0.526 | 0.526 | 0.526 | 0.526 | 0.526 |
| Allantoin | 0.1 | 0 | 0.1 | 0 | 0.1 |
| Panthenol (powder) | 0.5 | 0.5 | 0.5 | 5.0 | 0.5 |
| Tocopherol Acetate | 0.5 | 0.5 | 0.5 | 0.5 | 0.5 |
| Sodium Ascorbyl phosphate | 0.91 | 0.91 | 0.91 | 0.91 | 0.91 |
| Sodium Pyrophosphate | 0.5 | 0.5 | 0.5 | 0.5 | 0.5 |
| Preservatives | 0.15 | 0.15 | 0.5 | 0.5 | 0.15 |
| Flavorant | 1.03 | 1.03 | 1.03 | 1.03 | 1.03 |
| Water and Minors (e.g. Coloring Agent) | Q.S. | Q.S. | Q.S. | Q.S. | Q.S. |
| Total | 100 | 100 | 100 | 100 | 100 |

*Sodium hyaluronate having weight average molecular weight of ~1,400,000 Da.

Example B: Viscosity and Mucoadhesion Data

The viscosity profiles of the Inventive Example 1 and several benchmark products available from market (Examples 6 to 9) are tested according to the Rheological Test described hereinabove. The results of consistency coefficient K and the rate index n are listed in Table 2 below.

The mucoadhesion of the inventive example and the benchmark products (Examples 6 to 8) are tested by using the Mucoadhesion Test described hereinabove. The results are also summarized in Table 2 below.

TABLE 2

Viscosity & Mucoadhesion of Inventive Example 1 vs. Benchmark Products

| Example Nos. | Product Brand | Viscosity Consistency Coefficient K (Pa · s) | Rate Index n | Mucoadhesion Index (FI %) |
|---|---|---|---|---|
| Example 1 (Inventive) | | 78.4 | 0.370 | 2.923 |
| Example 6 (Comparative) | Sunstar Gel [i] | 12.3 | 0.567 | 0.386 |
| Example 7 (Comparative) | Gengigel Gel [ii] | 45.9 | 0.628 | 0.512 |
| Example 8 (Comparative) | Lion Ointment [iii] | 275 | 0.218 | 3.393 |
| Example 9 (Comparative) | Lion Gel [iv] | 1.95 | 0.396 | — |

[i] Sunstar G•U•M Interdental Gel (20160426) 13 ml
[ii] Gengigel Gingival Gel (1811121) 20 ml
[iii] Lion DENT HEALTH R Perio Care Gel Ointment (62431) 10 g
[iv] Lion DENT.EX Syatema Interdental Gel (150214NC) 20 ml Table 2 shows the viscosity and the mucoadhesion values of the Inventive Example 1 and the benchmark products. It can be seen from the results that the inventive Example 1 exhibits a desirable viscosity. The Comparative Example 6 (Sunstar Gel), the Comparative Example 7 (Gengigel Gel) and the Comparative Example 9 (Lion Gel) all exhibit relatively low viscosity profile which indicate undesirable retention or adhesion property. A gel with too low viscosity may flow too fast to adhere to or be retained on the user's gum. However, the comparative Example 8 (Lion Ointment) shows an extremely high viscosity profile, which indicates that such product has poor spreadability, i.e. too thick to be spread evenly on oral tissue surface.

It can also be seen from the mucoadhesion results that, both the Comparative Example 6 (Sunstar Gel) and the Comparative Example 7 (Gengigel Gel) show relatively low FI % which means their mucoadhesion is weaker. Inventive Example 1 exhibits a relatively stronger mucoadhesion, so that the leave-on gel product of the present invention provides a preferred retention property. The comparative Example 8 (Lion Ointment) also shows a strong mucoadhesion. However it is not capable of easily applied or spread along gum line due to its non-preferred overly high viscosity profile.

Example C: Consumer Sensory Test

Consumer Sensory Tests are conducted to measure the preference of consumer towards the Inventive Example 1 vs. the benchmark products (Examples 6 to 9).

Groups of qualified consumers are instructed for use of a series test product with unawareness of the product identity i.e. brand, ingredients, etc. A questionnaire was designed to get consumer rating on direct questions (DQs), including (1) whether the product is easy to disperse/spread on gum; (2) whether the product shows consistency on thickness/tackiness; and (3) whether the product stay enough time on gum. The rankings that the consumers give are divided into three levels, where "+++" means more than 60% of consumers preferred, "++" means more than 40% but less than 60% preferred, and "+" means that less than 40% consumers preferred. The inventive Example 1 is scored as "+++" for each of the aspects, exceeding the comparative Examples 6 to 9 overall. Comparative Example 8 (Lion Ointment) shows a preferred retention property, which is in accordance with the result in above mucoadhesive test. However, it has undesired spread ability and consistency on thickness/tackiness.

TABLE 3

Consumer Sensory Test Results

| Questionnaires | Example 1 Inventive | Example 6 | Example 7 | Example 8 | Example 9 |
|---|---|---|---|---|---|
| (1) Ease to apply and spread to gums | +++ | ++ | ++ | + | + |
| (2) Consistency on thickness and tackiness of gel | +++ | + | + | + | ++ |
| (3) Retention of gel to stay on gums | +++ | + | + | +++ | + |

"+++": >60% preferred
"++": 40~60% preferred
"+": <40% preferred

Example D: Assay for Measuring Improve Gingival Health in the Oral Cavity

The following assay is used to determine improved gingival wound healing in the oral cavity for the oral care compositions of the present invention and controls. The assay involves gentle probing of gingival crevice to assess presence or absence of bleeding. Gingivitis is assessed according to the Mazza modification of the Papillary Bleeding Index ("PBI", and according to Muhlemann, H. R.: *J. Prev. Dent.* 1977; 4:6), otherwise referred to as the "Mazza Index" to determine the number of bleeding sites (as defined by Mazza, 1981). For this measurement, probing is done on the mesiofacial and the distolingual surface of each tooth, at a maximum of 56 sites. The probe is placed in the gingival sulcus to a depth of approximately 0.5 mm to 1.0 mm and swept along the soft tissue aspect of the sulcus from its insertion point to the tip of the interdental papilla. All facial or lingual surfaces of each quadrant are swept before measurements are made. The measurements are made beginning with the first tooth swept.

Oral soft tissue and gingivitis examination using the Mazza Index are conducted at specified time points and assessed according to Mazza Index as defined as in Table 4.

TABLE 4

Mazza Index for Measuring Gingival Bleeding

| Score | Description |
|---|---|
| 0 | Normal appearing gingival (i.e., no color change), and no bleeding upon probing. |
| 1 | Color change related to inflammation, but no bleeding on probing. |
| 2 | Slight bleeding at the point of probing. |
| 3 | Bleeding extending from the point of probing and flowing around the gingival margin. |
| 4 | Profuse bleeding that overflows the gingival margin. |
| 5 | Spontaneous bleeding without probing. |

Experiments are conducted at Procter & Gamble (Beijing) Technology Co., Ltd. Oral Care Department, with approval from the P&G Beijing Technical Center (China) Institutional Review Board and in accordance with the World Medical Association Declaration of Helsinki (1996 amendment). ICH Guidelines for Good Clinical Practice ("GCP") are followed.

To start, subjects who met the study entrance requirement are randomly assigned to treatment or control groups balanced on Baseline Mazza Index scores using a SAS randomization program. Individuals meeting the following criteria are included: be at least 18 years of age; possess a minimum of 18 natural anterior teeth; have at least 10 bleeding sites as measured by Mazza Index at initial visit (i.e., Baseline); have gingivitis but not periodontitis; be in good general health as determined by the Investigator/designee based on a review of the medical history/update for participation in the study. Clinical parameters for each subject are monitored across the whole study. Individuals that fell into the exclusion criteria are excluded from study participation.

Study 1—Improving Gingival Health Using Stannous Containing Dentifrice Over 4-Week Study Period A 4-week, randomized, controlled and single-blinded study involving around 150 qualified subjects as described hereinabove. Subjects are treated with products from: [A] Experimental Group Stannous Containing Toothpaste (Lot FEO-FM-002) & Example 1 (inventive oral care composition), [B] Positive control group Stannous Containing Toothpaste (Lot FEO-FM-002), and [C] Negative control group (Regular fluoridated toothpaste product (e.g., 0.321% sodium fluoride-Crest® Cavity Protection Product, Lot Number 20170614B71651864AB, "CCP Product"). All assigned toothpastes are used to brush whole teeth thoroughly for 2 mins, twice daily morning and night. The subjects that have the additional oral gel treatment with inventive Ex. 1 following each toothpaste brushing step, would rinse mouth with 20 ml water for 30 seconds, then distributed 1 gram of composition Ex 1. on finger and applied topically to the teeth/gingival surface and refrain from food, drink and smoking for 1 hour. Mazza Index assessments are performed on the subjects to score for reduction of bleeding sites at Baseline, Week 1 and at 4 weeks (i.e., end of the study). The data are analyzed with analysis of covariance ("ANCOVA"), with the respective Baseline as the model covariate using the Statistical Analysis System ("SAS"). The results in terms of the number of bleeding sites, based on the Mazza Index, of the control groups and treatment group are averaged (as well as their confidence intervals) and defined in Table 5.

TABLE 5

Results for Bleeding Site Reduction Using Stannous-containing Toothpaste for 4 Weeks
Efficacy Results
Number of Bleeding Sites

| Treatment | N | Adj. Mean (SE) | Treatment Difference Versus [C] Crest Cavity Protection | 2-sided p-values versus [B] Oral-B Gum | 2-sided p-values versus [A] Oral-B & Composition Ex.1 |
|---|---|---|---|---|---|
| Week 1 (Baseline mean = 15.83) | | | | | |
| [C] Crest Cavity Protection | 50 | 14.413 (0.373) | | 0.0016 | <0.0001 |
| [B] Stannous-Containing Toothpaste | 50 | 12.783 (0.337) | 11.3% | | 0.0002 |
| [A] Stannous-Containing Tooth-paste & Composition Ex. 1 | 49 | 11.045 (0.283) | 23.4% | | |
| Week 4 (Baseline mean = 15.86) | | | | | |
| [C] Crest Cavity Protection | 50 | 14.058 (0.470) | | <0.0001 | <0.0001 |
| [B] Stannous-Containing Toothpaste | 50 | 9.313 (0.369) | 33.8% | | <0.0001 |

TABLE 5-continued

Results for Bleeding Site Reduction Using Stannous-containing Toothpaste for 4 Weeks
Efficacy Results
Number of Bleeding Sites

| Treatment | N | Adj. Mean (SE) | Treatment Difference Versus [C] Crest Cavity Protection | 2-sided p-values versus [B] Oral-B Gum | [A] Oral-B & Composition Ex.1 |
|---|---|---|---|---|---|
| [A] Stannous-Containing Toothpaste & Composition Ex. 1 | 49 | 7.036 (0.326) | 50.0% | | |

The results demonstrate that the stannous-containing toothpaste provides significant gingivitis reduction benefit vs. negative control of the fluoridated toothpaste. The additional application of the gel composition (Inventive Ex 1) provides further and significant gingivitis reduction benefit against the positive control of stannous-containing toothpaste alone and further significant improvement against the negative control.

Study 2—Improving Gingival Health with Regular Dentifrice Oral Hygiene Over 20-Day Study Period A 20-day, randomised, controlled and single-blinded study involving around 160 subjects that have been using Yunnan Baiyao, Sensodyne, Crest, Oral-B or other Gum Health toothpaste (i.e., Brand Used Most Often or BUMO) in at least the past 3 months. Subjects are treated with products from: (1) Experimental Group regular BUMO toothpaste+Example 1 (inventive oral care composition Lot EXP-17-AF-1469-E, with gum massage applicator), (2) Control group regular BUMO toothpaste. All subjects in both groups use their regular BUMO toothpaste and maintained brushing habits, twice daily morning and night. Subjects assigned to the experimental group, additionally post brushing, distributed 0.25 gram of inventive oral are composition on gum massage applicator and applied topically to upper teeth/gingival, both lingual and facial surface for 1 minute. The procedure is repeated, whereby 0.25 gram of the Inventive oral care composition Ex 1., distributed to the gum massager and applied topically to the lower teeth/gingival, both lingual and facial surface and refrained from food, drink and smoking for 1 hour. Mazza Index assessments are performed on the subjects to score for reduction of bleeding sites at Baseline, Day 3 and at Day 20 (i.e., end of the study). The data are analyzed with analysis of covariance ("ANCOVA"), with the respective Baseline as the model covariate using the Statistical Analysis System ("SAS"). The results in terms of the number of bleeding sites, based on the Mazza Index, of the control groups and treatment group are averaged (as well as their confidence intervals) and defined in Table 6.

TABLE 6

Results for Bleeding Site Reduction Using Regular Toothpaste Habit for 20 Days
Efficacy Results
Number of Bleeding Sites

| Treatment | N | Adj. Mean (SE) | Treatment Difference Versus [A] Regular BUMO Toothpaste | 2-sided p-values versus [A] Regular BUMO Toothpaste |
|---|---|---|---|---|
| Day 3 (Baseline mean = 16.23) | | | | |
| [B] Regular BUMO Toothpaste | 79 | 15.262 (0.421) | | <0.0001 |
| [A] Regular BUMO Toothpaste & Composition Ex. 1 | 79 | 12.611 (0.278) | 17.4% | |
| Day 20 (Baseline mean = 16.11) | | | | |
| [B] Regular BUMO Toothpaste | 79 | 13.968 (0.410) | | <0.0001 |
| [A] Regular BUMO Toothpaste & Composition Ex. 1 | 79 | 8.519 (0.305) | 39.0% | |

The results demonstrate that the regular oral hygiene group with additional application of the oral composition (Inventive Ex 1) provides rapid and significant gingivitis reduction benefit vs. regular oral hygiene alone at day 3 and the benefit further increased at day 20.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An oral care composition comprising:
   (a) from about 0.2% to about 2%, by weight of the oral care composition, of a hyaluronic acid or a salt thereof, wherein the hyaluronic acid has a weight average molecular weight of from about 900,000 Daltons to about 2,000,000 Daltons,
   (b) from about 0.1% to about 5%, by weight of the composition, of a polyacrylic acid, and
   (c) a total water content of from 30% to 65%, by weight of the composition,
   wherein the composition has a Viscosity Consistency Coefficient K of from about 50 Pa·s to about 250 Pa·s as measured at 22° C. at a shear rate range of 0.1-10s$^{-1}$,
   wherein the oral care composition has a Mucoadhesion Index of no less than about 0.6 Fluorescent Intensity Percentage ("FI%"), and
   wherein the oral care composition is a leave-on gel.

2. The oral care composition according to claim 1, wherein the Viscosity Consistency Coefficient K is from about 50 Pa·s to about 200 Pa·s.

3. The oral care composition according to claim 1, wherein the Mucoadhesion Index is no less than about 0.8 FI%.

4. The oral care composition according to claim 1, further comprising an additional polymer, wherein the additional polymer is selected from the group consisting of xanthan gum, carrageenan, carboxymethyl cellulose, hydroxyethyl cellulose, hydroxypropyl cellulose, hydroxymethyl cellulose, polyvinyl pyrrolidine, co-polymers of maleic anhydride with methyl vinyl ether having a weight average molecular weight of about 30,000 Daltons to about 1,000,000 Daltons, and combinations thereof; wherein the additional polymer is present in an amount of from about 0.1% to about 10%, by weight of the composition.

5. The oral care composition according to claim 1, wherein the oral care composition is substantially free of abrasives.

6. The oral care composition according to claim 1, further comprising a vitamin, wherein the vitamin is selected from the group consisting of Vitamin C, Vitamin E, Vitamin B5, and combinations thereof.

7. A method of improving Gum Health of a subject, the method comprising the steps of applying the oral care composition of claim 1 onto intraoral tissue of the subject, and leaving the oral care composition on the intraoral tissue without removal for a duration of time from about 1 minute to about 1000 minutes; and optionally wherein the applying step is the last step of an oral hygiene regimen.

8. The method of claim 7, wherein the oral care composition is applied to intraoral tissue with an applicator comprising a handle and a head to spread the oral care composition onto the intraoral tissue of the subject.

9. A method of improving Gum Health of a subject, the method comprising the steps of:
   (a) brushing teeth of the subject with an antibacterial toothpaste; and
   (b) subsequently, applying the oral care composition of claim 1 onto intraoral tissue of the subject, and leaving the oral care composition on the intraoral tissue without removal for a duration of time of at least about 2 minutes.

10. The method of claim 9, wherein the oral care composition is applied to intraoral tissue with an applicator comprising a handle and a head to spread the oral care composition onto the intraoral tissue of the subject.

11. A kit comprising a toothpaste and the oral care composition according to claim 1.

12. A kit comprising the oral care composition according to claim 1, and a delivery carrier for applying the oral care composition to intraoral tissue, wherein the delivery carrier comprises strip, film of material, dental tray, aligner, sponge material, applicator, or mixtures thereof.

* * * * *